United States Patent
Rhinehart et al.

(10) Patent No.: US 8,133,205 B2
(45) Date of Patent: Mar. 13, 2012

(54) FLUID DELIVERY SYSTEM HAVING A PLURALITY OF RESILIENT PRESSURIZING CHAMBERS

(75) Inventors: Edward J. Rhinehart, Monroeville, PA (US); Dennis P. Hack, Cheswick, PA (US); David M. Reilly, Glenshaw, PA (US); John F. Kalafut, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 376 days.

(21) Appl. No.: 11/942,772

(22) Filed: Nov. 20, 2007

(65) Prior Publication Data

US 2008/0071220 A1 Mar. 20, 2008

Related U.S. Application Data

(62) Division of application No. 11/072,999, filed on Mar. 4, 2005, now abandoned.

(51) Int. Cl.
*A61M 1/00* (2006.01)
(52) U.S. Cl. .......................... 604/151; 604/131; 604/153
(58) Field of Classification Search .................. 604/118, 604/121, 131, 132, 151, 152, 153, 154, 251
See application file for complete search history.

(56) References Cited

U.S. PATENT DOCUMENTS

| | | |
|---|---|---|
| 4,332,246 A | 6/1982 | Thomson |
| 4,886,504 A | 12/1989 | Arvidson et al. |
| 5,429,485 A | 7/1995 | Dodge |
| 5,806,519 A | 9/1998 | Evans, III et al. |
| 5,840,026 A | 11/1998 | Uber, III et al. |
| 5,843,037 A | 12/1998 | Uber, III |
| 5,916,197 A | 6/1999 | Reilly et al. |
| 5,924,852 A * | 7/1999 | Moubayed et al. ........... 417/474 |
| 6,068,617 A * | 5/2000 | Richmond ..................... 604/255 |
| 6,096,011 A | 8/2000 | Trombley, III et al. |
| 6,197,000 B1 | 3/2001 | Reilly et al. |
| 6,440,107 B1 | 8/2002 | Trombley, III et al. |
| 6,471,674 B1 | 10/2002 | Emig et al. |
| 6,623,455 B2 | 9/2003 | Small et al. |
| 6,643,537 B1 | 11/2003 | Zatezalo et al. |
| 6,699,219 B2 | 3/2004 | Emig et al. |
| 6,743,202 B2 | 6/2004 | Hirschman et al. |
| 7,713,239 B2 | 5/2010 | Uber, III et al. |
| 2002/0128606 A1 | 9/2002 | Cowan et al. |
| 2003/0014035 A1 | 1/2003 | Trombley, III et al. |
| 2003/0065287 A1 | 4/2003 | Spohn et al. |
| 2004/0064041 A1 | 4/2004 | Lazzaro et al. |

OTHER PUBLICATIONS

International Search Report from corresponding PCT WO06/007030, May 2007.

* cited by examiner

*Primary Examiner* — Bhisma Mehta
(74) *Attorney, Agent, or Firm* — Jill Denesvich

(57) ABSTRACT

A fluid delivery system includes a fluid container, two or more pressurizing chambers in fluid connection with the fluid container, a drive mechanism in operative connection with the two or more pressurizing chambers to pump fluid from the fluid container and an outlet in fluid connection with the two or more pressurizing chambers. Each of the two or more pressurizing chambers is formed from a flexible, resilient material that is adapted to be compressed to pressurize fluid therewithin.

21 Claims, 12 Drawing Sheets

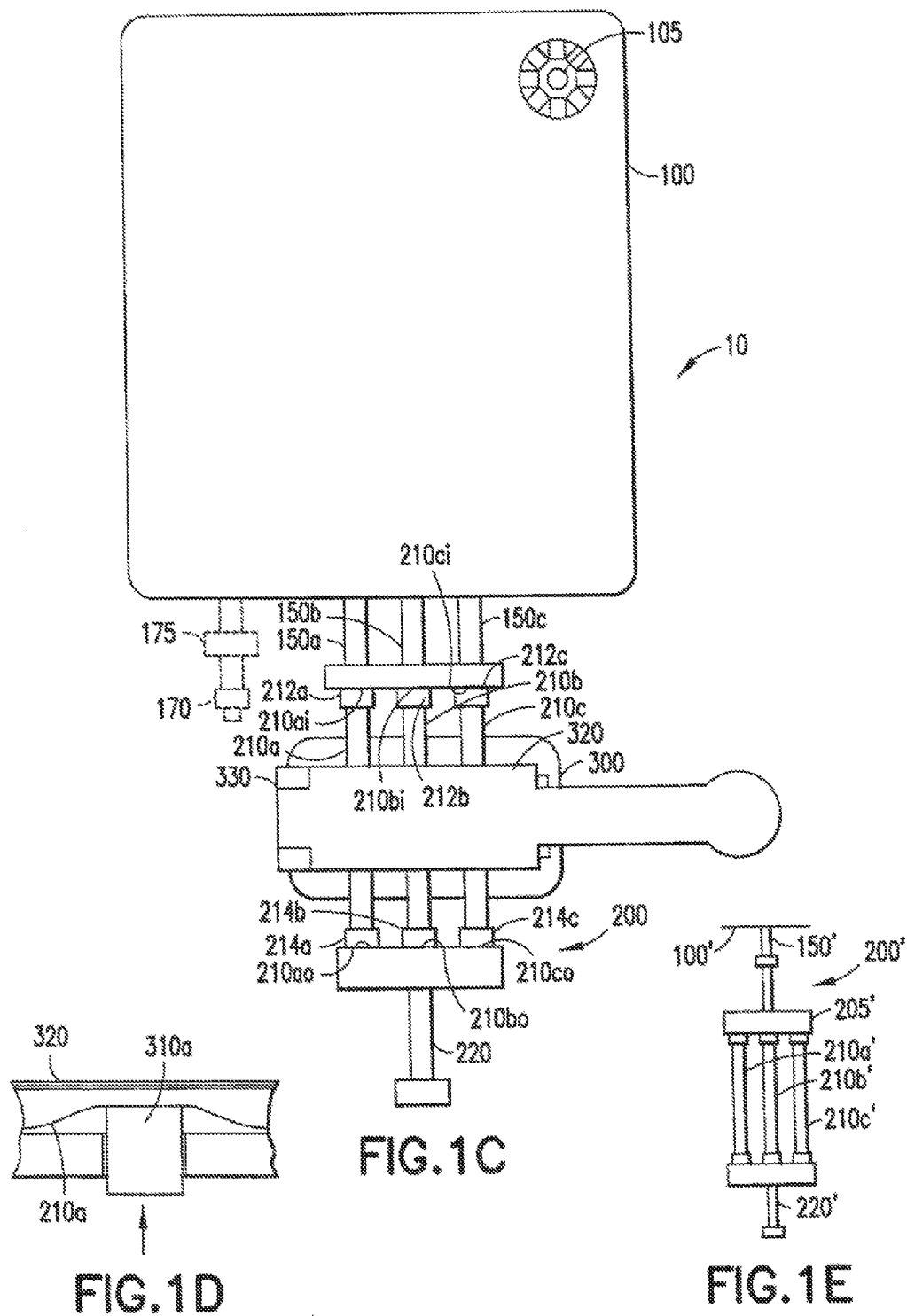

Fig. 2A
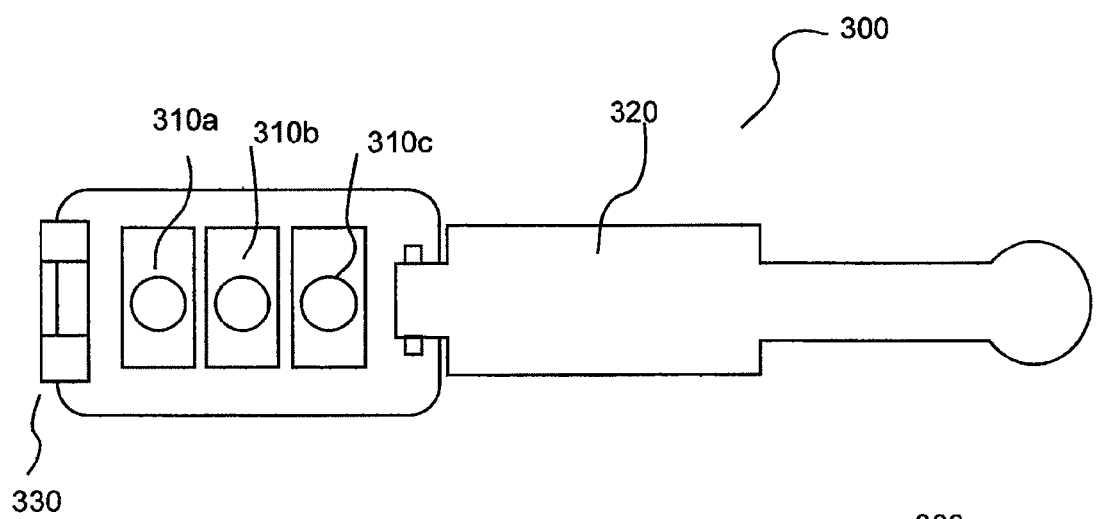
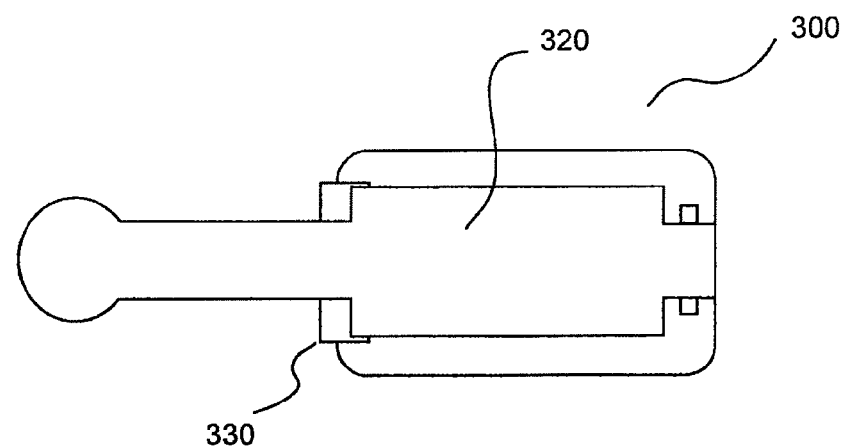
Fig. 2B

FLUID DELIVERY SYSTEM HAVING A PLURALITY OF RESILIENT PRESSURIZING CHAMBERS

CROSS REFERENCE TO RELATED APPLICATIONS

This application is a continuation of U.S. patent application Ser. No. 11/072,999, filed on Apr. 4, 2005, now abandoned, the contents of which are incorporated herein by reference.

BACKGROUND OF THE INVENTION

The present invention relates generally to fluid delivery systems, to fluid delivery devices and to methods of fluid delivery, and, especially, to fluid delivery systems, devices and method for delivery of medical fluids to a patient.

In many medical procedures, such as drug delivery, it is desirable to inject a fluid into a patient. Likewise, numerous types of contrast media (often referred to simply as contrast) are injected into a patient for many diagnostic and therapeutic imaging procedures. For example, contrast media are used in diagnostic procedures such as X-ray procedures (including, for example, angiography, venography and urography), computed tomography (CT) scanning, magnetic resonance imaging (MRI), and ultrasonic imaging. Contrast media are also used during therapeutic procedures, including, for example, angioplasty and other interventional radiological procedures as well as chemotherapy. Saline is often used as a diluent or flushing fluid in conjunction with contrast media. Regardless of the type of procedure, any fluid injected into the patient must be sterile and contain a minimum of pyrogens. Moreover, injection of air should be minimized or completely eliminated.

Under the typical current practice of injecting contrast media via syringe pumping systems using loadable, empty syringes, hospitals must purchase and stock many contrast media concentrations in multiple container sizes in an attempt to provide the correct concentration and amount of a specific contrast for a specific procedure, while minimizing the wastage of contrast. In that regard, contrast is typically very expensive. Most contrast media are thus provided by manufacturers in numerous concentrations in sterilized containers (such as glass bottles or plastic packages) ranging, for example, incrementally in size from 20 ml to 500 ml (and even up to 1000 ml under current European practice). These containers are generally designed for a single use (that is, once a container is opened for a patient, it is used for that patient only). The contrast is generally aspirated from such containers via the syringe pump used to inject the contrast, and any contrast remaining in the container is discarded to prevent infection with potentially contaminated contrast. The hospital staff is faced with the task of choosing an appropriately sized contrast container to assure an optimum study while minimizing discarded contrast. Time consuming procedures are required to reload the syringe if more contrast is required than originally calculated. On the other hand, expensive waste results if only a portion of a filled syringe is injected. The inventory of contrast containers required under the current system increases costs and regulatory burdens throughout the contrast media supplier-consumer chain.

Alternatively, contrast is provided in prefilled syringes which can be loaded onto an injector without time-consuming filling procedures. However, such syringes are provided in single-dose volumes. The hospital must still maintain an inventory of disposable syringes of different volumes and concentration. Moreover, hospital staff is still required to choose a prefilled syringe of appropriate volume to ensure that sufficient contrast is available during the injection procedure. Waste occurs if the prefilled syringe includes excess fluid. Waste also occurs, for example, in the case that a prefilled syringe includes insufficient fluid, resulting in termination of a procedure or use of only a portion of a second prefilled syringe.

Many of the costs, regulatory burdens and other problems associated with the use of multiple contrast containers, and even prefilled syringes, can be substantially eliminated through use of relatively large contrast media containers for single- and multiple-patient use in connection with a pumping system allowing any volume and concentration (as limited by the volume and concentration of the medial container) of contrast to be injected as determined by the hospital staff before or during a procedure. Relatively large containers of a fluid such as saline can be used for flushing and/or dilution. U.S. Pat. Nos. 5,916,197 and 6,197,000, assigned to the assignee of the present invention, the disclosures of which are incorporated herein by reference, disclose pumping systems that are removably connectable to a relatively large source of contrast or saline. Those pumping systems are adapted to provide controlled, continuous flow of generally any volume of fluid during an injection procedure.

Although continuous pumping systems such as disclosed in U.S. Pat. Nos. 5,916,197 and 6,197,000 can eliminate many of the problems associated with current injection practices, a number of problems persist. For example, there is a risk of contamination by operating personnel when removable fluid connections are made or broken (such as the fluid connection between a fluid source and the pumping mechanism of the pumping system). Making such fluid connections also requires use of valuable and limited operator time. Furthermore, required operator tasks introduce the potential for human error.

It thus remains desirable to develop improved fluid delivery systems, fluid delivery devices and methods of fluid delivery.

SUMMARY OF THE INVENTION

In one aspect, the present invention provides a fluid delivery system including at least one container for fluid to be delivered to a patient, a continuous pumping mechanism in non-removable fluid connection with the container, and an outlet in fluid connection with the pumping mechanism. The container can be a flexible container (for example, a flexible plastic bag) or a rigid container (for example, a glass container).

In general, the continuous pumping mechanisms of the present invention enable convenient operation via continuous (or uninterrupted) pumping of fluid from the container (without, for example, having to stop and reload) over multiple procedures and/or patients. Moreover, a patient dose can be determined in real time as the procedure is progressing, ensuring that the patient will be neither over dosed nor under dosed. Moreover, no waste of fluids occurs as a result of over dosing or under dosing.

In general, the continuous pumping mechanisms suitable for use in the present invention are energy assisted devices (for example, electrical energy, mechanical energy, manual energy, pneumatic energy etc.) as opposed to, for example, gravity fed or drip devices. Examples of continuous pumps suitable for use in the present invention include, but are not limited to, rotary pumps, multi-chambered piston pumps and gear pumps. In certain embodiments, positive displacement pumps are preferred. In positive displacement of the liquid medium, there is generally a one-to-one correspondence between the length of a stroke (typically, a generally linear stroke) of a pressurizing mechanism and the amount of liquid medium displaced. Positive displacement through generally linear motion can, for example, provide better volumetric efficiency than achievable through the use of rotational or rotary pumps. Volumetric efficiency can be defined as the volume of fluid actually per unit mechanical displacement divided by the theoretical volume of fluid delivered per unit mechanical displacement. The volumetric efficiency of rotational pumps can be dependent upon the pressure and flow rate of the liquid medium. In certain embodiments, multi-chambered, positive displacement pumps are preferred.

Continuous pumping mechanisms for use in the present invention are preferably capable of achieving relatively high flow rates (for example, flow rates in excess of 0.1 ml/second and often in the range of approximately 0.1 ml/second to 50 ml/second) and/or high pressure (for example, in excess of 20 psi) injections without excessive pulsatile flow. Typically, high flow rates are associated with high pressures as a result of delivery of such high flow rates through relatively small-bore flow path elements (for example, catheters).

Preferably, continuous pumping mechanisms for use in the present invention provide for relatively accurate control of a bolus of fluid delivered to a patient (for example, rise and fall times of under 100 ms can be provided in the case of, for example, a square bolus). A square bolus of fluid delivery or other bolus configuration may be required for optimum enhancement.

The continuous pumping mechanisms of the present invention facilitate closed feedback control during fluid delivery. For example, based on the measured results of the fluid already delivered, fluid delivery parameters (for example, flow rate, volume, concentration etc.) can be readily adjusted in real time based on the measure real time results. The continuous pumping mechanisms of the present invention can also preferably provide for relatively accurate control of the delivery of fluids. (for example, within ±2% of volume and flow rate, and within ±50 psi of pressure controlled) over a broad range of flow rates.

The fluid delivery system of the present invention can further include at least one one-way valve or other mechanism in fluid connection with the container (for example, between the pumping mechanism and the container) to prevent flow of fluids from outside the container into the container (for example, from the pumping mechanism into the container). In one embodiment, the container includes a plurality of ports in fluid connection with the pumping mechanism, and a one way valve is in fluid connection between the pumping mechanism and each the plurality of ports, to prevent flow from the pumping mechanism to the container. Preventing flow of fluid from outside of the container into the container (for example, from the pumping mechanism to the container) can reduce the likelihood of cross-contamination between patients when the fluid delivery systems of the present invention are used in connection with multiple patients. Likewise, undesirable fluids (for example, air or, indeed, any fluid other than the original contents of the container can be prevented from entering the container. Additionally or alternatively, the pumping mechanism is adapted (for example, via means known in the pumping arts) so that it cannot pump fluid from outside the container into the container. In other words, the pumping mechanism cannot be operated in reverse. Preventing such reverse flow can further reduce or eliminate the likelihood of cross-contamination between patients and reduce the likelihood of drawing fluids (for example, air) into the container. Preferably, continuous pumping mechanisms used in the present invention facilitate generally the prevention of or the minimization of delivery of air to a patient during an injection procedure.

In one embodiment, the pumping mechanism includes at least one pressurizing chamber in fluid connection with the container. The pressurizing chamber is adapted to be placed in operative, removable connection with an energy assisted drive mechanism to pump fluid from within the container. As described above, fluid from the container can, for example, be pressurized within the pressurizing chamber via positive displacement. The pumping mechanism can include a plurality of pressurizing chambers in which fluid from the container is pressurized for delivery to the patient via positive displacement. In one embodiment, each of the pressurizing chambers is in fluid connection with a single pumping mechanism outlet.

The pressurizing chambers can, for example, be formed from a flexible, resilient material that can be compressed to pressurize fluid within the pressurizing chamber. The flexible material of the pressurizing chambers can be suitably resilient such that recovery of the flexible material of the pressurizing chambers creates a pressure difference between the pressurizing chamber and the storage container suitable to draw fluid from the storage container into the pressurizing chambers.

In another embodiment, each of the pressurizing chambers comprises a piston slidably disposed therein.

The container of the present invention can, for example, filled with fluid to be injected and be substantially devoid of air (for example, when shipped to the end user). For example, the volume of air in the container can be less than 1 volume percent. Additionally or alternatively, the end user can simply purge air from the container as known in the medical injection arts.

In one embodiment, the container comprises no inlet port through which a fluid can enter the container. In this manner, contamination of fluid within the container with external agents can more easily be prevented. However, such inlet ports can be provided in certain embodiments. The fluid container and the pumping mechanism of the fluid delivery systems of the present invention can, for example, be disposable as unit.

The outlet of the pumping mechanism can, for example, be placed in fluid connection with a connector adapted to place the fluid delivery system in fluid connection with a per-patient disposable tubing set. The connector can, for example, be adapted to place the pumping mechanism in fluid connection with a plurality of per-patient disposable tubing sets sequentially to allow injection of fluid from the container into multiple patients. The connector can, for example, be swabable to clean the connector after a tubing set has been removed therefore and prior to connection of another tubing set thereto.

In another aspect, the present invention provides a fluid delivery system, including: at least one container for fluid to be delivered to a patient, a drive mechanism, and a continuous pumping mechanism in non-removable fluid connection with the fluid container. The pumping mechanism is adapted to be placed in removable, operative connection with the drive mechanism. The fluid delivery system further comprises an outlet in fluid connection with the pumping mechanism.

As described above, the fluid delivery system can further include at least one one-way valve in fluid connection between the pumping mechanism and the container to prevent flow from the pumping mechanism to the container. In one embodiment, the pumping mechanism includes a plurality of pressurizing chambers in which fluid from the container is pressurized at least one one-way valve in fluid connection between the pumping mechanism and the container to prevent flow from the pumping mechanism to the container. Likewise, the pumping mechanism can be adapted to not pump fluid from outside the container into the container.

Each of the pressurizing chambers can be in fluid connection with a single pumping mechanism outlet. In one embodiment, the pressurizing chambers are formed from a flexible, resilient material that can be compressed to pressurize fluid within the pressurizing chamber. The flexible material of the pressurizing chambers can be suitably resilient such that recovery of the flexible material of the pressurizing chambers creates a pressure difference between the pressurizing chamber and the storage container suitable to draw fluid from the storage container into the pressurizing chambers. The drive mechanism can include at least one drive member to compress the pressurizing chambers. The drive mechanism can, for example, include a drive member for each of the pressurizing chambers to compress each of the pressurizing chambers in a timed fashion. The operation of the drive member can be appropriately timed to reduce pulsatile nature of the flow.

In another embodiment, each of the pressurizing chambers includes a piston slidably disposed therein. In this embodiment, the pumping mechanism can, for example, include a plurality of connectors wherein one of the plurality of connectors is in operative connection with each of the pistons. Each of the plurality of connectors is adapted to be placed in releasable connection with the drive mechanism. The drive mechanism can, for example, include a plurality of drive members. Each of the plurality of drive member can include a cooperating connector adapted to be placed in removable, operative connection with one of the connectors of the pumping mechanism.

In another aspect, the present invention provides a method of distributing a fluid to be injected into a patient, including the step of creating a fluid delivery system by filling at least one container with fluid to be to be injected into at least one patient. The fluid container is placed in non-removable fluid connection with a continuous pumping mechanism (as described above). The pumping mechanism includes an outlet. The method further includes transporting the fluid delivery system to a user.

The pumping mechanism can be in non-removable fluid connection with container prior to filling the container. The pumping mechanism can also placed in non-removable fluid connection with container after filling the container.

The method can further include the step of priming the pumping mechanism with fluid from the container prior to transporting the fluid delivery system. The method can also include the step of purging air from at least the container of the fluid delivery system prior to transporting the fluid delivery system.

The method can further include the step of placing the fluid delivery system in a package prior to transporting the fluid delivery system. The fluid delivery system can be packaged in a sterile state.

In another aspect, the present invention provides a method of delivery fluid to a patient, including the step of removing a fluid delivery system from a package. The fluid delivery system includes: at least one container having therein fluid to be delivered to a patient, a continuous pumping mechanism in non-removable fluid connection with the container, and an outlet in fluid connection with the pumping mechanism. The method further includes the steps of removably connecting the pumping mechanism to a drive mechanism and connecting a first patient interface to the outlet.

The method can further include injecting fluid into at least a first patient. The method can also include the step of removing the first patient interface from connection with the outlet after injecting fluid into the first patient and connecting a second patient interface to the outlet. The method can further include the step of disposing of the fluid delivery system after injecting fluid therefrom.

In a further aspect, the present invention provides a kit for fluid delivery packaged in a sterile container. The kit includes at least one fluid delivery system including: at least one container for fluid to be delivered to a patient, a continuous pumping mechanism in non-removable fluid connection with the container, and an outlet in fluid connection with the pumping mechanism. The kit can further include at least one per-patient disposable tubing set including a connector to connect to the outlet of the fluid delivery system. A plurality of per-patient disposable tubing sets can be provided. The kit can also include at least one manual syringe connectable to the tubing set. The manual syringe can, for example, be adapted to draw blood from a patient or to inject a fluid.

A plurality of fluid delivery systems, wherein each of the fluid delivery systems includes a different fluid in the container thereof, can be included in the system. In one embodiment, the container of one of the fluid delivery systems encloses a contrast enhancement medium and the container of another one of the fluid delivery systems encloses saline.

In an additional aspect, the present invention provides a fluid delivery device, including: at least one inlet connectable to a fluid supply and at least two resilient pressurizing chambers in fluid connection with the at least one inlet. Each of the pressurizing chambers is formed from a flexible material that can be compressed to pressurize fluid within the pressurizing chamber. The fluid delivery system further includes an inlet valve in fluid connection with each of the pressurizing chambers between the storage container and the pressurizing chamber. The inlet valve is operable to allow fluid to enter the pressurizing chamber from the storage container but to prevent fluid from flowing from the pressurizing chamber into the storage container. A common outlet is in fluid connection with the pressurizing chambers. An outlet valve is in fluid connection with each of the pressurizing chambers between the pressurizing chamber and the outlet. The outlet valve is operable to allow fluid to enter the outlet from the pressurizing chamber but to prevent fluid from flowing from the outlet into the pressurizing chamber.

In another aspect, the present invention provides a fluid delivery system including: at least one container for fluid to be delivered to a patient and a pumping mechanism in non-removable fluid connection with the container. The pumping mechanism is suitable to pressurize the fluid to at least 20 psi. The fluid delivery system further includes an outlet in fluid connection with the pumping mechanism. In one embodiment, the pumping mechanism is suitable to pressurize the fluid to at least 50 psi. In another embodiment, the pumping mechanism is suitable to pressurize the fluid to at least 100 psi. In still another embodiment, the pumping mechanism is suitable to pressurize the fluid to at least 300 psi.

In a further aspect, the present invention provides a fluid delivery system including: at least one container for fluid to be delivered to a patient; a pumping mechanism in non-removable fluid connection with the container. The pumping mechanism is suitable to pressurize the fluid with a degree of pulsatile flow no greater than 25%, wherein the degree of pulsatile flow is defined by the following equation:

$$100\% * (\text{max flow} - \text{min flow})/\text{average flow}.$$

The fluid delivery system further includes an outlet in fluid connection with the pumping mechanism. In one embodiment, the degree of pulsatile flow is no greater than 20%. In another embodiment, the degree of pulsatile flow is no greater than 15%. In still another embodiment, the degree of pulsatile flow is no greater than 10%.

In another aspect, the present invention provides a fluid delivery system including: at least one container for fluid to be delivered to a patient. The container has a single port. The fluid delivery system further includes a pumping mechanism in non-removable fluid connection with the single port of the container and a mechanism adapted to prevent reverse flow through the pump and into the container via the single port.

In another aspect, the present invention provides a fluid delivery system including: at least one container for fluid to be delivered to a patient; a pumping mechanism in non-removable fluid connection with the container, and an outlet in fluid connection with the pumping mechanism. The container can, for example, include less than 1% by volume of air. In one embodiment, the container has less than 3 ml of air therein.

BRIEF DESCRIPTION OF THE DRAWINGS

Other aspects of the invention and their advantages will be discerned from the following detailed description when read in connection with the accompanying drawings, in which:

FIG. 1C illustrates the fluid delivery system of FIG. 1A in operative connection with the drive mechanism.

FIG. 1D illustrates an enlarged view of one of the drive members of the drive mechanism of FIG. 1A compressing a pressurizing chamber of the pumping mechanism of the fluid delivery system of FIG. 1A.

FIG. 1E illustrates an alternative embodiment of a pumping mechanism of the present invention which operates in a manner similar to the pumping mechanism of FIG. 1A but includes a single inlet in fluid connection with the fluid container.

FIG. 2A illustrates the drive mechanism of FIG. 1A in an open state in which the pumping mechanism can be place in operative connection therewith.

FIG. 2B illustrates the drive mechanism of FIG. 1A in a closed state.

DETAILED DESCRIPTION OF THE INVENTION

Figure 1A:
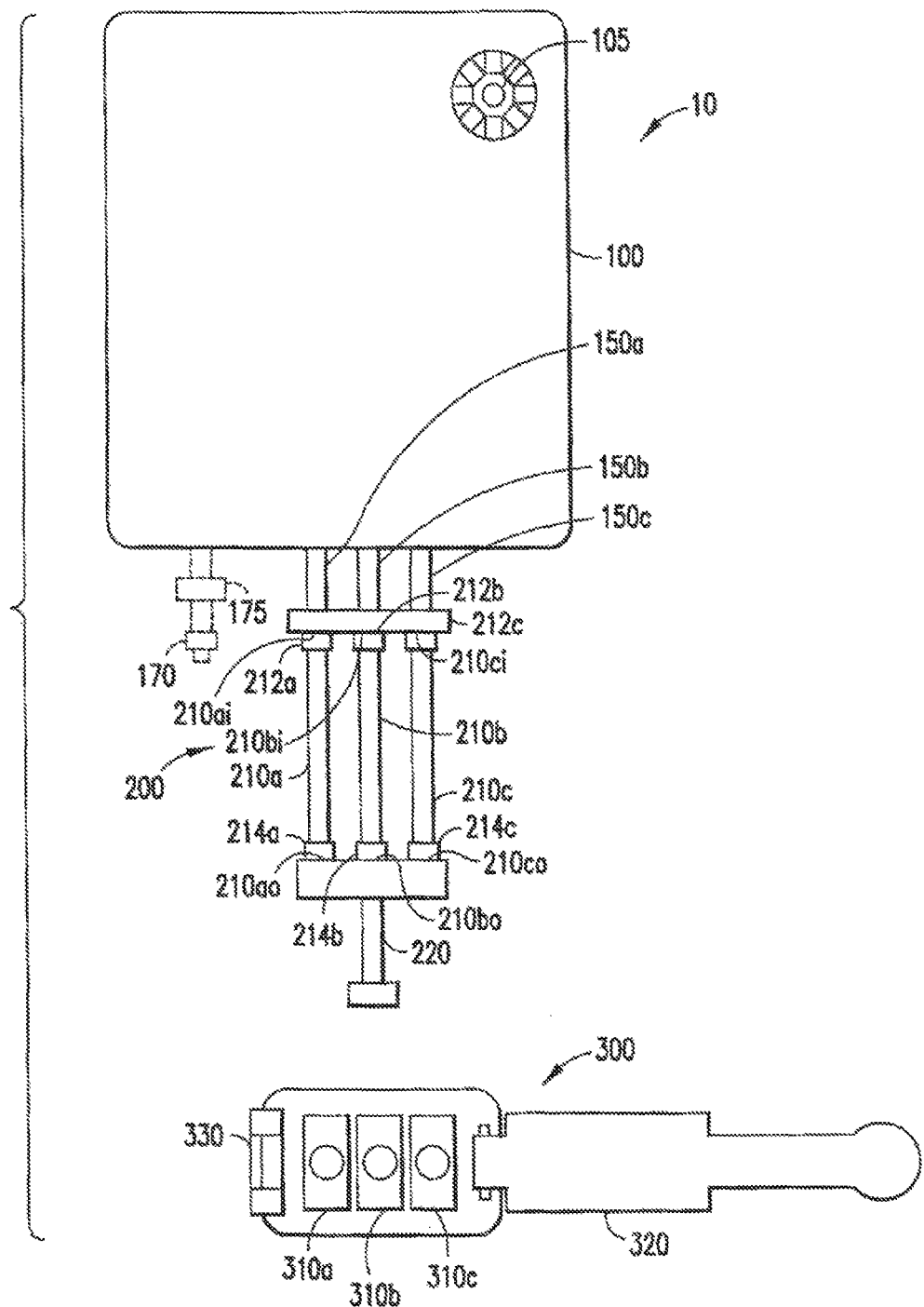
FIG. 1A illustrates an embodiment of a fluid delivery system of the present invention and an embodiment of a drive mechanism for use with the pumping mechanism of the fluid delivery system of FIG. 1A.
Figure 1B:
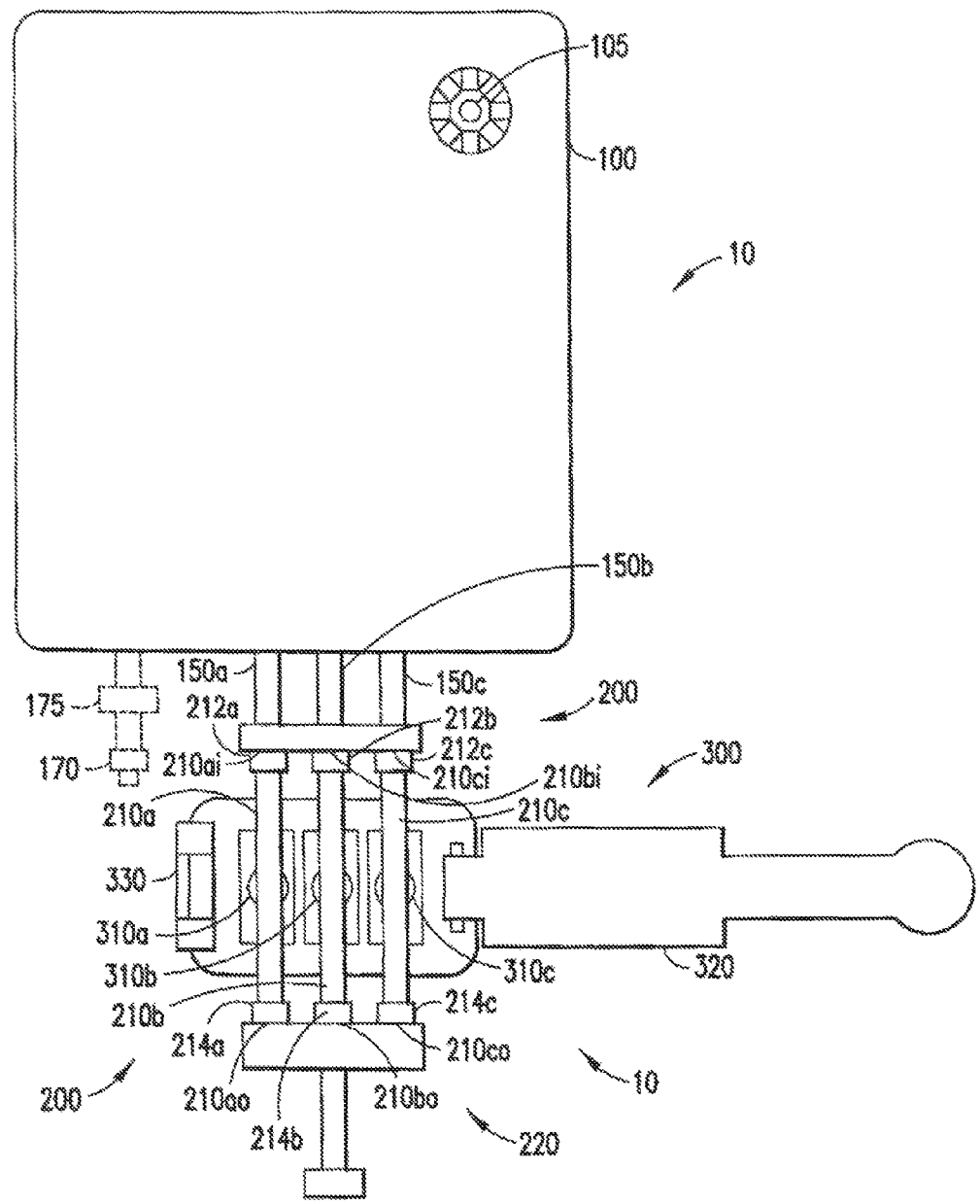
FIG. 1B illustrates the fluid delivery system of FIG. 1A in position to be in operative connection with the drive mechanism.

In general, the present invention provides fluid delivery systems that can be used to inject one or more fluids into one or more patients. FIGS. 1A through 1D illustrate an embodiment of a fluid delivery system 10 of the present invention in which a fluid container 100 is in operative connection with a continuous pumping mechanism 200 including multiple pressurizing chambers. In the embodiment of FIGS. 1A through 1C, pumping mechanism 200 includes three generally parallel pressurizing chambers 210a, 210b and 210c forming separate generally parallel flow paths through the pumping mechanism 200. System 10 further includes an actuator or drive mechanism 300, which operates in connection with pumping mechanism 200 to pump fluid from within fluid container 100.

In one embodiment, each of pressurizing chambers 210a, 210b and 210c is formed from a flexible, resilient material such as a resilient polymeric material (for example, silicone polymer materials, urethane polymer materials and vinyl polymer materials), each having an input 210ai, 210bi and 210ci for fluid connection to the fluid container 100. Drive mechanism 300 includes drive members 310a, 310b and 310c, which cooperate with chambers 210a, 210b and 210c, respectively, to pressurize fluid within chambers 210a, 210b and 210c. In that regard, drive members 310a, 310b and 310c operate in a reciprocating manner (similar to a piston) to compress (see FIG. 1D) chambers 210a, 210b and 210c in an alternating, timed manner or sequence to provide continuous flow from a common outlet 220, which is in fluid connection with each of chambers 210a, 210b and 210c via respective outputs 210ao, 210bo and 210co of the chambers 210a, 210b and 210c. Preferably, the compression of the pressurizing chambers is timed to reduce pulsatile nature of the resultant flow. Control of pumping mechanisms including multiple pressurizing chambers to reduce pulsatile flow is further discussed below in connection with the fluid delivery system of FIGS. 4A through 5.

Drive mechanism 300 includes a closure 320 which is illustrated in an open state in FIGS. 1A and 1B. During use, an operator positions chambers 210a, 210b and 210c in operative connection with drive mechanism 300 so that each of chambers 210a, 210b and 210c are positioned adjacent drive members 310a, 310b and 310c, respectively, as illustrated, for example, in FIG. 1B. The operator then rotates closure 320 to a closed state as illustrated in FIG. 1C. A latch or lock mechanism 330 cooperates with closure 320 to maintain closure 320 in a closed state. Drive mechanism 300 is also illustrated in an open state and a closed state (absent pumping mechanism 200) in FIGS. 2A and 2B, respectively.

In the embodiment of FIGS. 1A through 1D, container 100 is permanently or unremovably in fluid connection with pumping mechanism 200 via connective tubing segments 150a-c. As used herein, the terms "permanently" or "unremovably" do not mean that container 100 and pumping mechanism 200 must be in fluid connection under all conditions, but that container 100 and pumping mechanism 200 will remain in fluid connection under all normal condition (including, those conditions experienced during transporting and operating the fluid delivery system). One can, for example, cut tubing segments 150a-c or apply a very large force to tubing segments 150a-c to break the fluid connection between container 100 and pumping mechanism 200. However, such operations would not typically occur, even accidentally, during normal transport or operation. Moreover, such an operation would leave fluid delivery system 10 in a damaged state recognizable by an operator, who could discard the damaged fluid delivery system. Thus, under normal operation, an operator is not required to make any fluid path connections between container 100 and pumping mechanism 200 and cannot break any fluid connection between container 100 and pumping mechanism 200. Permanent connection can, for example, be effected by forming the pumping mechanism of the present invention integrally with the containers of the present invention or through the use of nonremovable connections of flow path element (using, for example, plastic welds, adhesives etc. as known in the art).

Container 100 can include a port 105 through which, for example, additional or other fluids can be injected into container 100. In many cases, however, it may be undesirable to allow fluid to be transferred into container 100. Introduction of fluid into container 100 after initial distribution thereof can, for example, introduce contaminant(s), introduce air, or result in injection of an incorrect or undesirable fluid (or fluid concentration). Moreover, it can be desirable to prevent liquids from entering container 100 to, for example, ensure that a known injection fluid composition is injected and to prevent "refilling" and/or reuse of container 100 (which can, for example, increase the risk of contamination). Container 100 can also include one or more outlet ports 170 through which fluid can pass out of container 100 to a destination other than pumping mechanism 200. Such ports 170 can include a one-way valve 175 to prevent fluid from passing therethrough into container 100.

In the embodiment of FIGS. 1A through 1D, inlet one-way valves (for example, duck-billed check valves) 212a, 212b and 212c are placed in fluid connection with pressurizing chambers 210a, 210b and 210c, respectively, to allow fluid to enter pressurizing chambers 210a, 210b and 210c from container 100, but to prevent fluid from flowing from pressurizing chambers 210a, 210b and 210c into container 100 Likewise, outlet one-way valves (for example, duck-billed check valves) 214a, 214b and 214c are placed in fluid connection with pressurizing chambers 210a, 210b and 210c, respectively, to allow fluid to flow from pressurizing chambers 210a, 210b and 210c to outlet 220, but to prevent fluid from flowing from outlet 220 into pressurizing chambers 210a, 210b and 210c. The one-way valve configuration described above facilitates pressurization of the fluid by pumping mechanism 200 and assists in preventing any bloodborne contaminants from one or more patients from entering pressurizing chamber 220. Other check valves can also be provided in fluid connection with outlet 220 to assist in preventing cross-contamination in cases that fluid delivery system is used in connection with multiple patients.

FIG. 1E illustrates an alternative embodiment of a pumping mechanism 200' similar, in many respects, in design and operation to pumping mechanism 200. Components of pumping mechanism 200' are numbered similarly to like components of pumping mechanism 200 with the addition of the designation "'". In the case of, pumping mechanism 200', pressurizing chambers 210a', 210b' and 210c' are in fluid connection with a manifold 205' that is in permanent or non-removable fluid connection with container 100' via a single tubing segment 150'.

Figure 3:
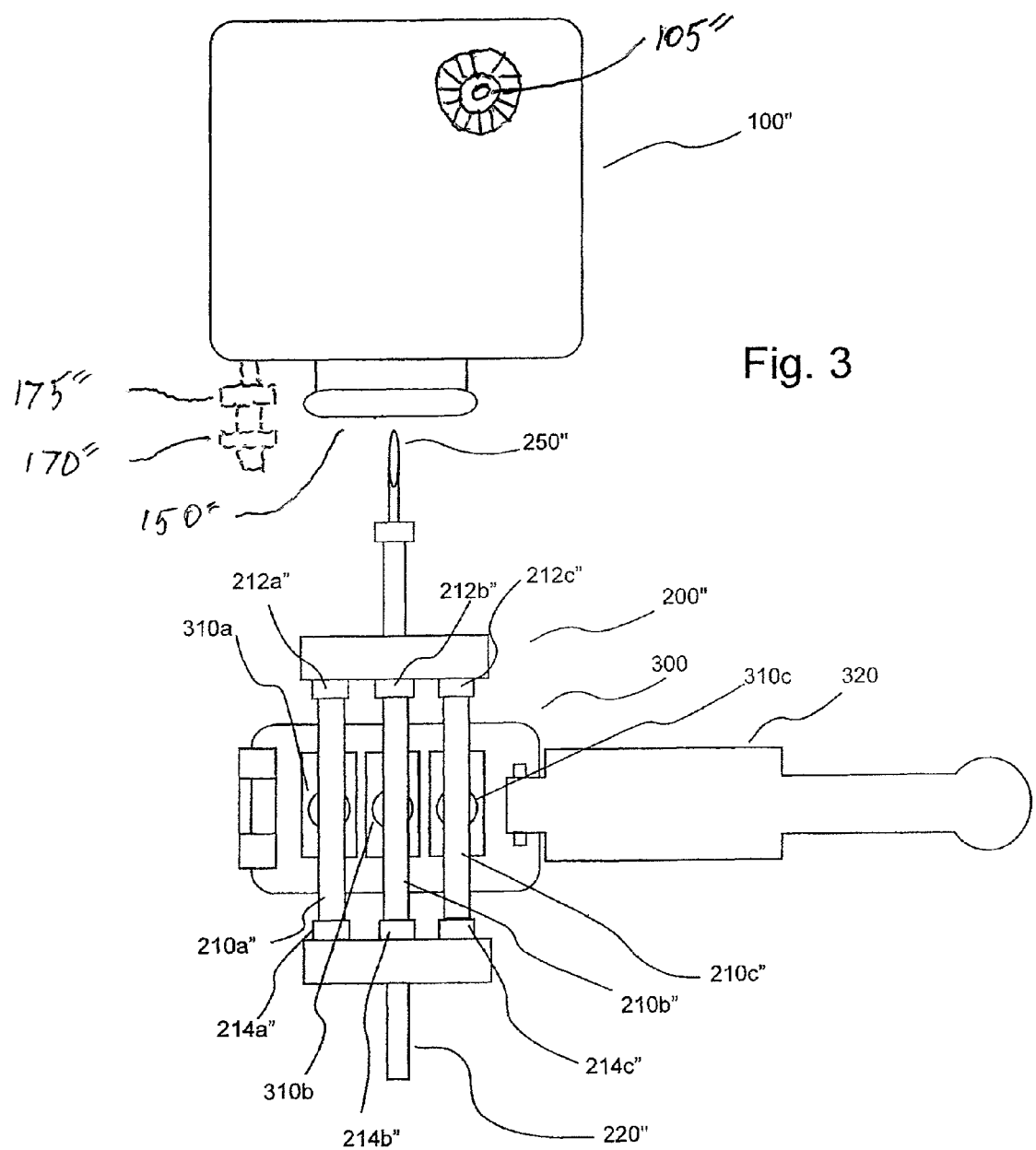
FIG. 3 illustrates another embodiment of a fluid delivery system of the present invention in which a pumping mechanism is connectable to a fluid container.

FIG. 3 illustrates an alternative embodiment of a pumping mechanism 200" similar in design and operation to pumping mechanism 200. Components of pumping mechanism 200" are numbered similarly to like components of pumping mechanism 200 with the addition of the designation "''". Unlike pumping mechanism 200, however, pumping mechanism 200" is disconnectible or removable from container 100". In the embodiment of FIG. 3, pumping mechanism 200" can be placed in fluid connection with container 100" via cooperation of a connector 250" in the form of a piercing member or spike, which cooperates with a cooperating connector in the form of a pierceable septum 150" on container 100" as known in the art. Further, container 100" can include a port 105" through which, for example, additional or other fluids can be injected into container 100". In many cases, however, it may be undesirable to allow fluid to be transferred into container 100". Introduction of fluid into container 100" after initial distribution thereof can, for example, introduce contaminant(s), introduce air, or result in injection of an incorrect or undesirable fluid (or fluid concentration). Moreover, it can be desirable to prevent liquids from entering container 100" to, for example, ensure that a known injection fluid composition is injected and to prevent "refilling" and/or reuse of container 100" (which can, for example, increase the risk of contamination). Container 100" can also include one or more outlet ports 170" through which fluid can pass out of container 100" to a destination other than pumping mechanism 200". Such ports 170" can include a one-way valve 175" to prevent fluid from passing therethrouqh into container 100".

Figure 4A:
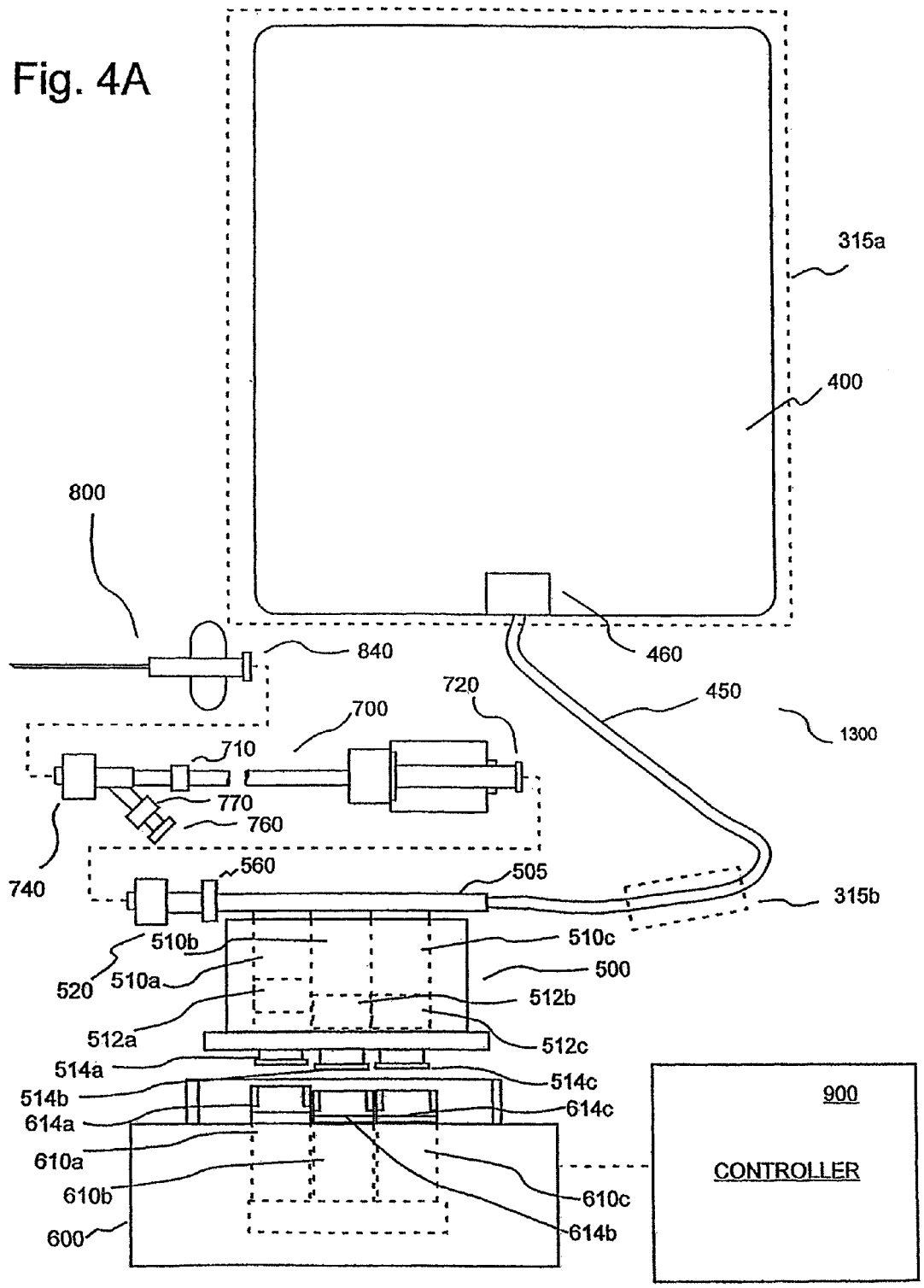
FIG. 4A illustrates another embodiment of a fluid delivery system of the present invention in which the pumping mechanism thereof includes a plurality of pressurizing chambers in which pistons are slidably positioned.
Figure 4B:
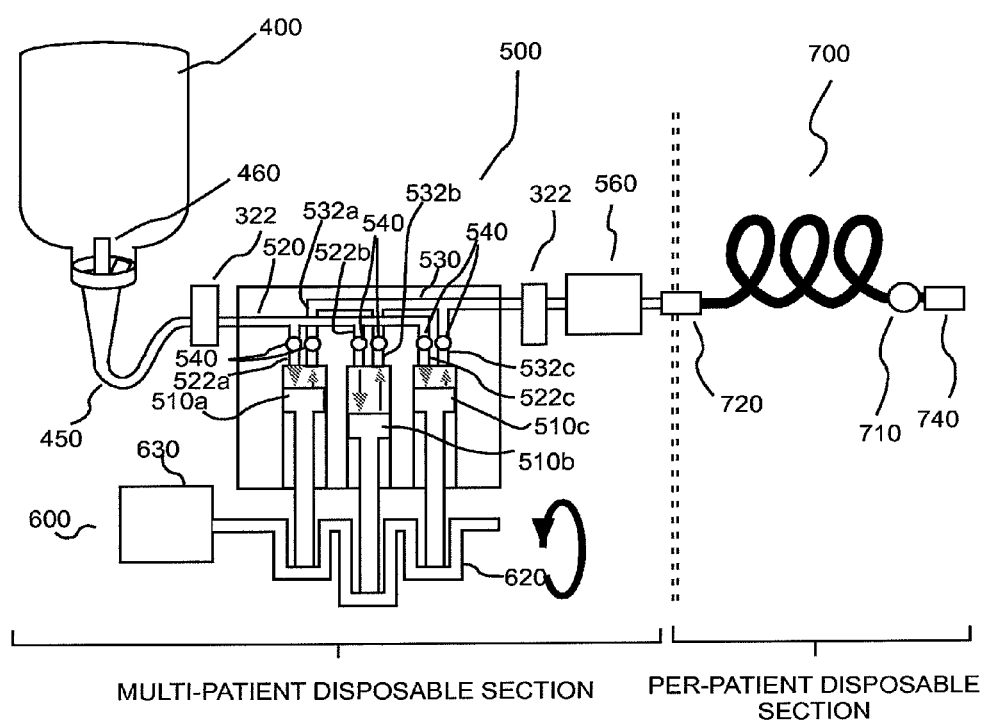
FIG. 4B illustrates a schematic drawing of the fluid delivery system of FIG. 4A showing a multi-patient disposable portion and a per-patient disposable portion.
Figure 5:
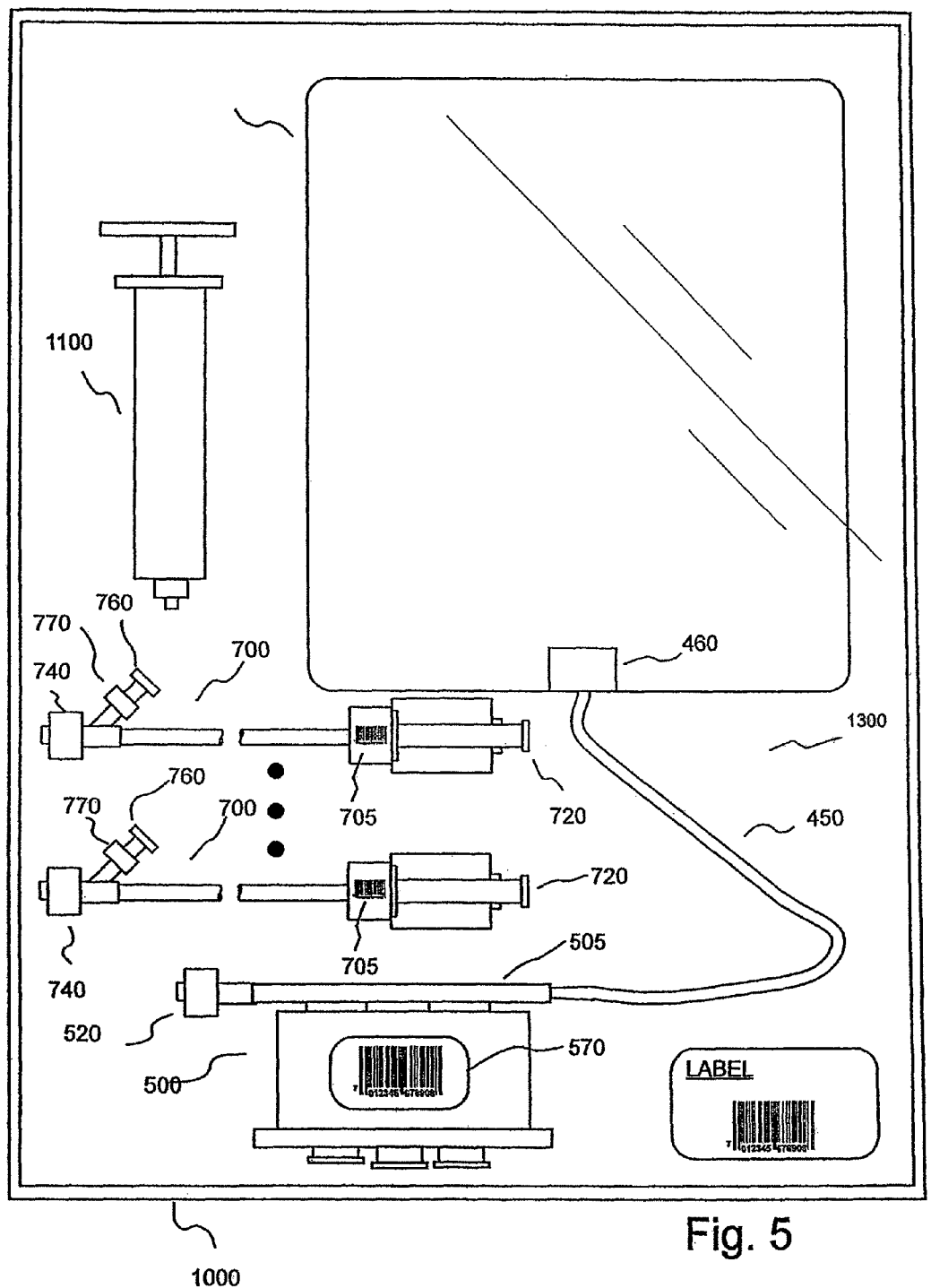
FIG. 5 illustrates a sterile packaged kit including the fluid delivery system of FIG. 4A.

FIGS. 4A through 5 illustrates another embodiment of a fluid delivery system 1300 of the present invention. Fluid delivery system 1300 includes a fluid container 400 in generally permanent or non-removable fluid connection with a pumping mechanism 500 via tubing 450. Pumping mechanism 500 operates essentially as set forth in U.S. Pat. Nos. 5,916,197 and 6,197,000, assigned to the assignee of the present invention, the disclosure of which is incorporated herein by reference.

Pumping mechanism 500 includes a plurality of pressurizing chambers. In the embodiment of FIGS. 4A through 5, pumping mechanism includes three pressurizing chambers 510a, 510b and 510c. Each of pressurizing chambers 510a, 510b and 510c includes a piston 512a, 512b and 512c, respectively, slidably disposed therein. Pistons 512a, 512b and 512c are in operative connection with connectors 514a, 514b and 514c which cooperate with connectors 614a, 614b and 614c, respectively, of a drive mechanism 600.

Connectors 614a, 614b and 614c are in operative connection with drive members 610a, 610b and 610c, respectively, of drive mechanism 600. As described in U.S. Pat. Nos. 5,916,197 and 6,197,000, drive members 610a, 610b and 610c can, for example, be actuated in a timed manner or sequence to reduce any pulsatile nature of the flow of fluid exiting pumping mechanism 500. Each drive member 610a, 610b and 610c can, for example, attached to a cam shaft 620 via bearing assemblies as described in U.S. Pat. Nos. 5,916, 197 and 6,197,000. Cam shaft 620 is in operative connection with a motor 630. Motor 630 or pumping mechanism 500 can, for example, include a mechanism (not shown) such as a mechanical or electrical stop mechanism in operative connection therewith to prevent operation of pumping mechanism 500 in a reverse direction (or a direction that would result in fluid flow into or towards container 400).

Figure 6:
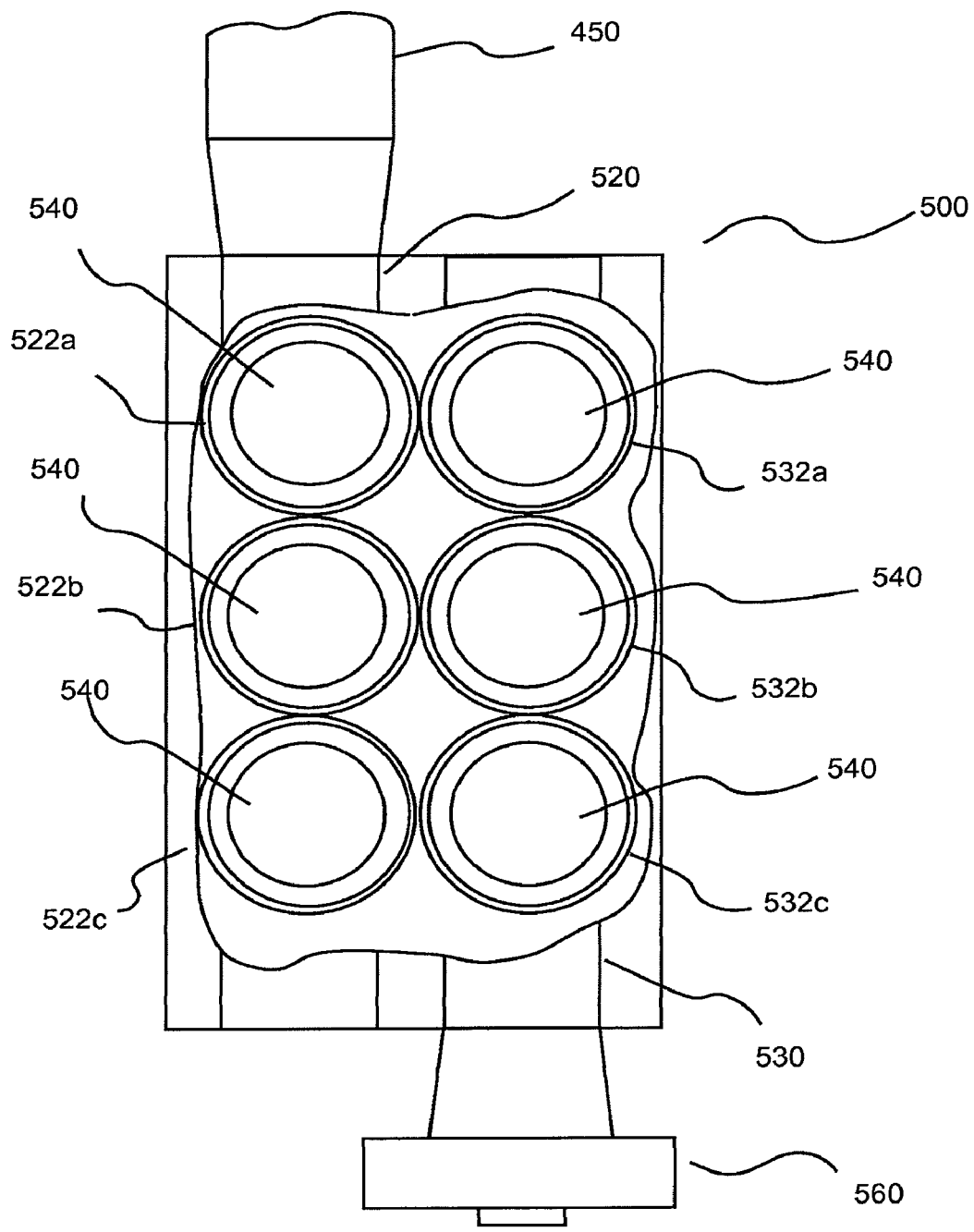
FIG. 6 illustrates a top, cutaway view of the pumping mechanism of the fluid delivery of FIG. 4A.

As also disclosed in U.S. Pat. Nos. 5,916,197 and 6,197,000, each pressurizing chamber 510a, 510b and 510c includes an inlet port 522a, 522b and 522c and an outlet port 532a, 532b and 532c, respectively (see FIGS. 4B and 6). Inlet ports 522a, 522b and 522c and outlet ports 532a, 532b and 532c are, for example, provided with one-way valves 540 to ensure the desired direction of flow is maintained. Inlet port 522a, 522b and 522c are in fluid connection with a common inlet channel 520 (which is in fluid connection with container 400 via tubing 450), while outlet port 532a, 532b and 532c are in fluid connection with a common outlet channel 530. Inlet channel 520 and outlet channel 530 are part of a head 505 (see, for example, FIG. 4A), which can, for example, be fabricated from an integral piece of polymeric material. One-way valves 540 used in connection with the inlet ports 522a, 522b and 522c and outlet ports 532a, 532b and 532c of pressurizing chambers 510a, 510b and 510c can, for example, include flexible disks that act as valves to allow unidirectional flow into or out of each pressurizing chamber. Flexible check valves 540 can, for example, be made of rubber or a lightweight polymer. Such one-way valves operate to prevent flow from pumping mechanism 500 toward container 400 via tubing 450.

Fluid delivery system 1300 is placed in fluid connection with a patient (not shown) via a per-patient disposable tubing or administration set 700. Tubing set 700 can, for example, include at least one connector 720 on a first end thereof that cooperates with a connector 560 on an outlet of pumping mechanism 500 to place tubing set 700 in removable fluid connection with pumping mechanism 500. A second end of tubing set 700 can include a connector 740 to form a connection with, for example, a catheter such as a butterfly catheter 800, which includes a cooperating connector 840. Connectors 560 and 720, as well as connectors 740 and 840 can, for example, be cooperating Luer connectors as known in the art.

Tubing set 700 can also be connected to pumping mechanism via a disconnectible aseptic connection (that is, connector sections 560 and 720 form a removable aseptic connection). For example, disconnectible aseptic connector suitable for use in the present invention are disclosed in U.S. Pat. Nos. 6,471,674 6,699,219 6,440,107 and 6,096,011, and Published U.S. Patent Application No. 2003/0014035 (Ser. No. 10/190,361), assigned to the assignee of the present invention, the disclosures of which are incorporated herein by reference. Use of such a disconnectible aseptic connection can, for example, facilitate use of fluid delivery system 1300 with multiple patients. In that regard, container 400 can be provided with sufficient fluid for use with multiple patients. In such an embodiment, a different per-patient disposable tubing set 700 can be used in connection with each patient. A one-way valve or check valve 710 can be placed in line near the outlet of tubing set 700 to prevent flow of fluid from a patient toward connector 720. After an injection procedure with a patient, tubing set 700 is removed from connection with pumping mechanism 500. Aseptic connector 560 (for example, a swabable valve) can, for example, be wiped with a antiseptic wipe prior to connection of a new tubing set 700 to reduce any risk of cross-contamination between patients. Subsequently, a new sterile tubing set 700 can be connected to pumping mechanism 500 via aseptic connection 560 and another injection procedure performed with a different patient. Fluid delivery set 1300 can, for example, be discarded after use with a predetermined number of patients (for example, ten patients).

Tubing sets 700 for use in the present invention can, for example, be provided with more than one connector 720 to enable connection of more than one fluid delivery system 1300 thereto. This can, for example, facilitate attachment of a second fluid delivery system to tubing set 700 if there is insufficient fluid in the first fluid delivery system to perform a specific injection with a patient. The second connector 720 (not shown, but identical to first connector 720), can include a protective cap to maintain the sterility thereof until use there may be required. Use of such a second connector in tubing set 700 can, for example, prevent waste of an amount of fluid in a particular fluid delivery system when the remaining fluid is insufficient to perform an injection procedure.

FIG. 5 illustrates fluid delivery system 1300 packaged in a sterile package 1000 for distribution. As illustrated, container 400 is in permanent fluid connection with pumping mechanism 500 via tubing 450 as shipped within sterile packaging 1000. In the embodiment of FIG. 5, a plurality of sterile per-patient disposable tubing sets 700 are include in package 1000 to, for example, facilitate use of fluid delivery system 1300 with multiple patients as described above. One of tubing sets 700 can, for example, be placed in sterile fluid connection with pumping mechanism 500 prior to distribution in package 1000. Package 1000 can also include a manual syringe 1100 which can, for example, be used to draw blood from a patient through a port 760 on tubing set 700 to confirm patency of catheter 800 within a patient's vein. In that regard, if flow through tubing set 700 cannot be reversed using pumping mechanism 500, syringe 1100 provides a simple mode of confirming patency. Port 760 can include a control valve 770 in fluid connection therewith to prevent fluid from exiting port 760 when tubing set 700 is under fluid pressure during an injection.

In one embodiment, the fluid container 400 is a flexible containers similar to a flexible fluid bag as known in the medical arts. With use of a flexible fluid container it is possible to substantially or even completely remove air from container 400 prior to distribution of fluid delivery system 400, thereby substantially reducing the risk of injecting large quantities of air into a patient. Container 400 can include an openable port 460 such as a tear-off or beak-off port as known in the art (available, for example, from Qosina Corp of Edgewood, N.Y.) that prevents fluid from flowing from container 400 into tubing 450 (or into container 400) until an operator opens port 460. Such a port can be placed inside container 400 or exterior to container 400 and in fluid connection with tubing 450. After port 460 is placed in an open state, an operator preferably primes tubing 450, pumping mechanism 500 and tubing set 700 to remove air therefrom by displacing such air with fluid from container 400. One or more air detectors 322 can also be placed in fluid connection with fluid delivery system 1300 and or tubing set 700 to provide further assurance that air is not injected into a patient.

As further illustrated in FIG. 4A, a controller 900 can be placed in operative communicative connection with drive mechanism 600. Examples of control of flow from multiple pharmaceutical fluid containers (including, syringes and other containers) is, for example, disclosed in U.S. Pat. Nos. 5,840,026, 6,643,537 and Published U.S. Patent Application No. 2004/0064041 (Ser. No. 10/159,592), assigned to the assignee of the present invention, the disclosures of which are incorporated herein by reference. Pumping mechanism 500 (and/or other system components such as container 400) can, for example, include one or more readable information stores or indicators 570 that can be read by, for example, controller 900 to provide information to controller 900 regarding the configuration of fluid delivery system 1300 (for example, fluid volume, fluid identity, concentration etc.) to facilitate control of drive mechanism 600. As illustrated in FIG. 5, information store 570 can for example be an optically readable bar code. Information store or indicator 570 can also, for example, be an RFID (radio frequency identification) tag as known in the art or other electrical or electromechanical coding system as known in the art. Coding systems used in connection with syringes that can also be used or adapted for use in connection with the fluid delivery systems of the present invention are, for example, disclosed in U.S. Patent No. 6,743,202 and Published U.S. Patent Application Nos. 2003/0065287 (Ser. No. 10/114,710), 2002/0128606 (Ser. No. 09/765,498) and 2004/0064101 (Ser. No. 10/466,418), assigned to the assignee of the present invention, the disclosures of which are incorporated herein by reference. Tubing set 700 can likewise include an information store or indicator 705 to provide information on the configuration thereof to controller 900. Such information (for example, volume information) can, for example, be used to enable an automated priming function in which pumping mechanism 500 and tubing set 700 are primed with activation of a single switch by an operator.

In addition to flow control, controller 900 can, for example, note when a fluid delivery system 1300 has been attached to drive mechanism 600 and begin countdown of a time period (for example, 24 hours) during which the fluid in container 400 must be injected or discarded. An alert can be provided or flow can be prevented (by, for example, flow controller 900 or other system element) after such time period. Flow Controller 900 can also provide an alert as to when there is insufficient fluid within container 400 to perform a specific injection procedure. At this point, a new or second fluid delivery system 1300 can be placed in fluid connection with tubing set 700 as described above to ensure that sufficient fluid is available for the injection procedure.

A bulk fluid heating system 315a (see, FIG. 4A) can be placed in operative connection with container 400 to heat the fluid to a temperature (for example, body temperature) to make the injection procedure more comfortable for a patient. Heating the fluid can also facility delivery by reducing viscosity. Alternatively or additionally an inline, real time heating system 315b can be placed in operative connection with the fluid path. In the embodiment, of FIG. 4A, heating system 315b is place in operative connection with tubing 450.

Figure 7:
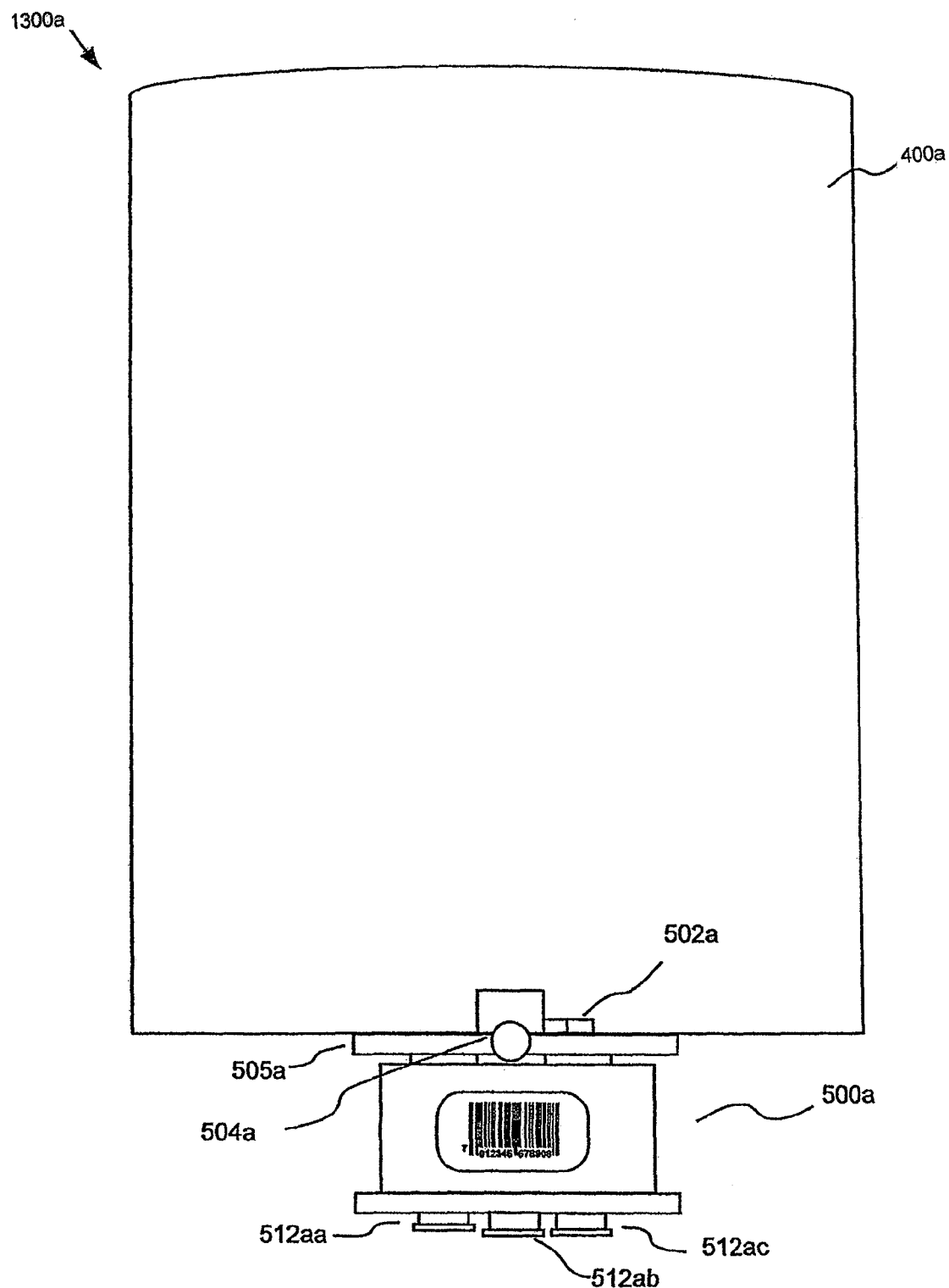
FIG. 7 illustrates an alternative embodiment of a fluid delivery system of the present invention, which operates similarly to the fluid delivery system of FIG. 4A, but in which the pumping mechanism is connected to the fluid container or source directly without intervening tubing.

FIG. 7 illustrates another embodiment of a fluid delivery system 1300a in which a pumping mechanism 500a, which operates substantially the same as pumping mechanism 500, is formed integrally with container 400a without intervening tubing. In that regard, an inlet 502a of head 505a of pumping mechanism 500a is in direct fluid connection with the interior of container 400a. Pumping mechanism outlet 504a can, for example, be in fluid connection with an aseptic connector as described above for connection of tubing set 700 thereto. Inlet 502a can include a break-off port as described above. Pumping mechanism 500a operates in connection with drive mechanism 600 via connectors 512aa, 512ab and 512ac, as described above in connection with pumping mechanism 500.

Figure 8:
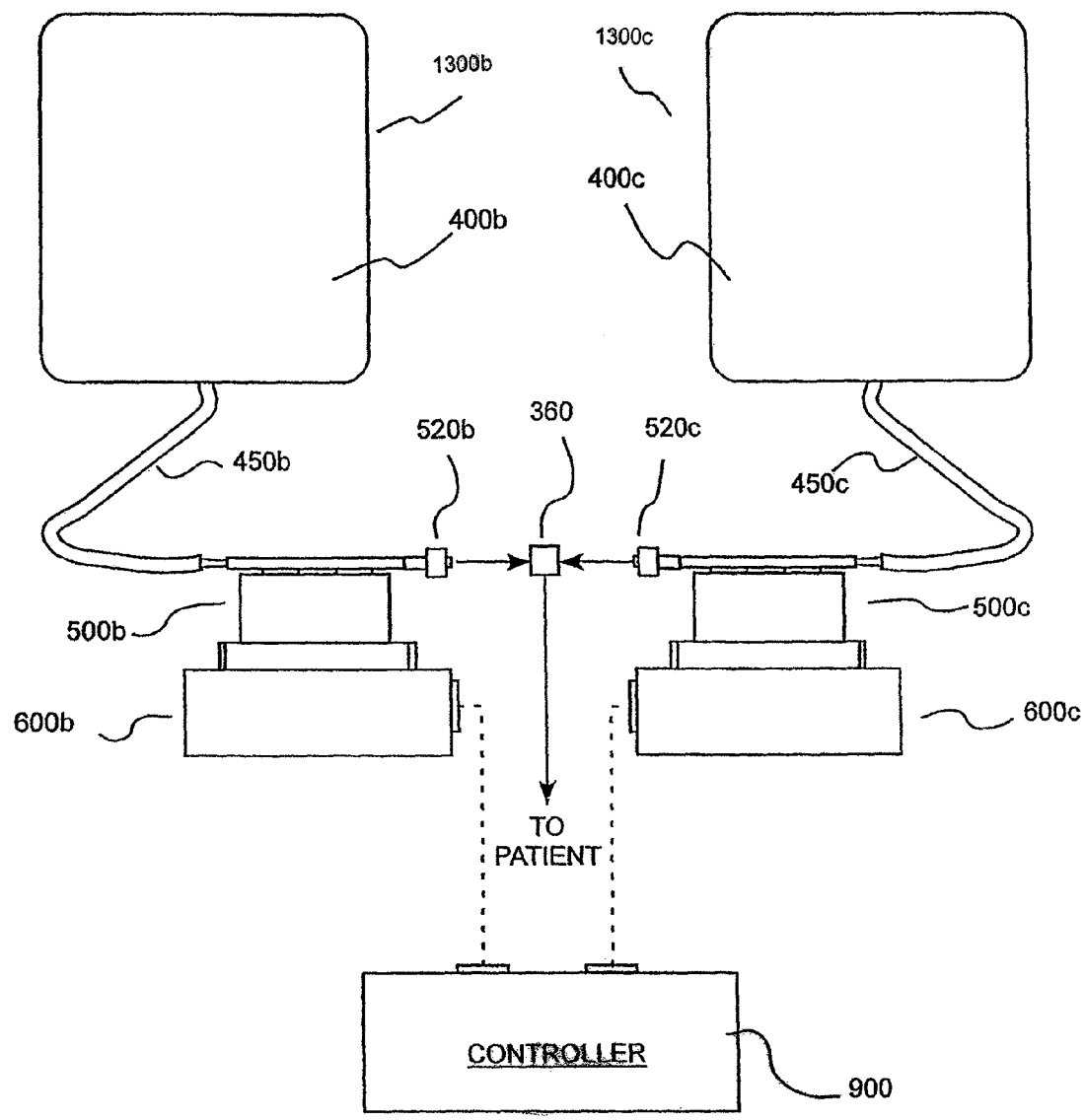
FIG. 8 illustrates the use of a plurality of fluid delivery systems of the present invention to inject multiple fluids into a patient.

In many injection procedures, it is desirable to inject two or more fluids into a patient (simultaneously or sequentially). For example, saline is often used in connection with a contrast medium. As illustrated in FIG. 8, multiple fluid delivery systems 1300b and 1300c (substantially identical to fluid delivery system 1300 with like components therewith numbered accordingly) can be provided to inject a plurality of fluids into a patient (for example, contrast and saline). Although two fluid delivery systems 1300b and 1300c are shown in FIG. 8, more than two such systems can be provided to inject three or more fluids into a patient during a single injection procedure. Such fluid delivery systems can be distributed in the same or different sterile packages as, for example, described in connection with FIG. 5. As clear to one skilled in the art, controller 900 can readily be used in connection with multiple fluid delivery systems of the present invention. In the embodiment, of FIG. 8, each of fluid delivery systems 1300b and 1300c are in fluid connection with a common mixing element or chamber 360, which can be place in fluid connection with a per-patient disposable tubing set as described above. Controller 900 can, for example, control (and vary) flow from each of fluid delivery systems 1300b and 1300c to control (and vary) total flow rate and relative concentration of each fluid during the course of an injection procedure.

Figure 9:
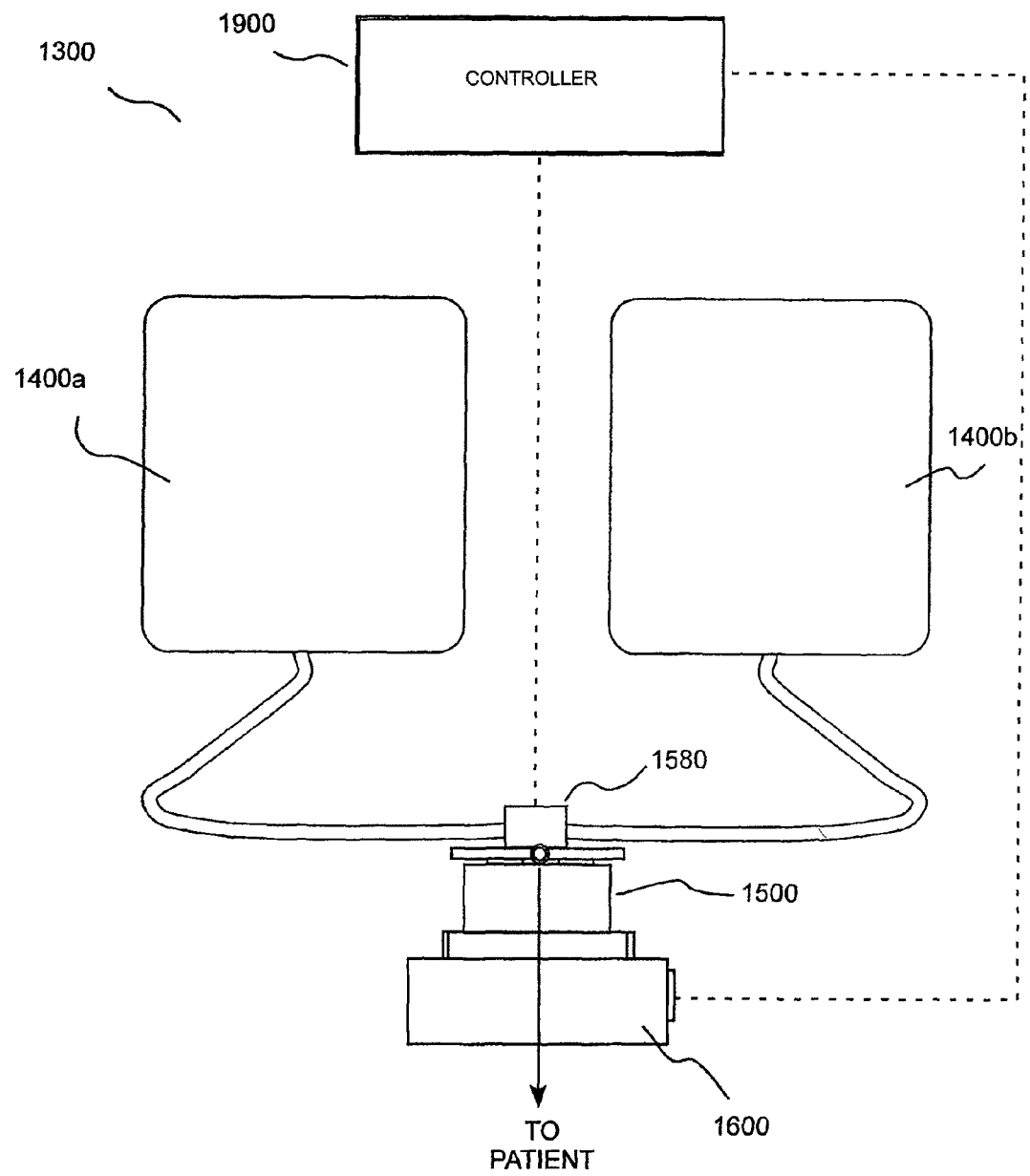
FIG. 9 illustrates another embodiment of a fluid delivery system of the present invention in which multiple fluid containers or sources are in fluid connection with a single pumping mechanism to inject multiple fluids into a patient.

In the embodiment of FIG. 9, a fluid delivery system 1300 is illustrated which includes a plurality of (that is, two or more) containers 1400a and 1400b which are connected to a single pumping mechanism 1500 via a multiport control valve 1580. Control valve 1580 and drive mechanism 1600 can, for example, be controlled via a controller 1900 to inject a desired amount of either of both of the fluids enclosed in containers 1400a and 1400b.

In the systems of the present invention, total fluid injection rate can be maintained constant or varied in virtually any manner while flow rate of the component fluids can be varied independently. An injection protocol including the parameters for the injection can be input into controller 900 based upon, for example, patient specific parameters. Moreover, feedback of one or more measured variables (for example, patient variables, measured contrast enhancement, etc.) can be used to alter the injection protocol in real time.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:
1. An injection system, comprising:
   a fluid container;
   a pumping mechanism comprising two or more pressurizing chambers in fluid connection with the fluid container via a connector, each of the two or more pressurizing chambers being formed from a flexible, resilient material that is adapted to be compressed to pressurize fluid therewithin,
   wherein each of the two or more pressurizing chambers has an input and an output, the input of each of the two or more pressurizing chambers in fluid connection with the fluid container, and
   wherein the two or more pressurizing chambers are disposed generally parallel to each other, to form separate flow paths through the pumping mechanism; and
   a drive mechanism comprising respective drive members cooperating with the two or more pressurizing chambers of the pumping mechanism to pump fluid from the fluid container and to pressurize fluid within the two or more pressurizing chambers, wherein the drive members are driven in a reciprocating manner to sequentially compress the respective pressurizing chambers in an alternating, timed sequence to sequentially pass fluid through the separate flow paths and provide substantially continuous fluid flow to an outlet in fluid connection with the output of each of the two or more pressurizing chambers.

2. The fluid delivery system of claim 1, further comprising a check valve in fluid connection with the outlet to prevent contaminants from entering into the pumping mechanism.

3. The fluid delivery system of claim 1, further comprising an inlet valve in fluid connection with each of the two or more pressurizing chambers, respectively, and adapted to allow flow from the fluid container into the two or more pressurizing chambers but to prevent flow from the two or more pressurizing chambers into the fluid container.

4. The fluid delivery system of claim 1, further comprising an outlet valve in fluid connection with each of the two or more pressurizing chambers, respectively, and adapted to allow flow from the two or more pressurizing chambers into the outlet but to prevent flow from the outlet into the two or more pressurizing chambers.

5. The fluid delivery system of claim 1 wherein the two or more pressurizing chambers comprises three pressurizing chambers.

6. The fluid delivery system of claim 1 wherein the fluid container comprises an inlet port through which additional fluid or another fluid can be delivered into the fluid container.

7. The fluid delivery system of claim 1 wherein the fluid container comprises one or more outlet ports through which fluid can be delivered to a destination other than the pumping mechanism.

8. The fluid delivery system of claim 1 wherein the drive mechanism further comprises a closure that is adapted to be moved between an open position and a closed position of the drive mechanism.

9. The fluid delivery system of claim 1 wherein the flexible material of the two or more pressurizing chambers is suitably resilient such that recovery of the flexible material creates a pressure difference between the two or more pressurizing chambers and the fluid container suitable to draw fluid from the fluid container into the two or more pressurizing chambers.

10. A fluid delivery system comprising:
a connector connectible to a fluid container;
at least two pressurizing chambers in fluid connection with the connector, each of the at least two pressurizing chambers being formed from a flexible, resilient material that can be compressed to pressurize fluid within the at least two pressurizing chambers,
wherein each of the at least two pressurizing chambers has an input and an output, the input of each of the at least two pressurizing chambers in fluid connection with the connector,
wherein the at least two pressurizing chambers are disposed generally parallel to each other to form separate flow paths,
a common outlet in fluid connection with the output of each of the at least two pressurizing chambers;
an inlet valve in fluid connection with each of the at least two pressurizing chambers, respectively, and operable to allow fluid to enter the at least two pressurizing chambers from the fluid container but to prevent fluid from flowing from the at least two pressurizing chambers into the fluid container;
an outlet valve in fluid connection with each of the at least two pressurizing chambers, respectively, and operable to allow fluid to enter the common outlet from the at least two pressurizing chambers but to prevent fluid from flowing from the common outlet into the at least two pressurizing chambers; and
a drive mechanism comprising respective drive members cooperating with at least two pressurizing chambers to pump fluid from the fluid container and to pressurize fluid within the at least two pressurizing chambers, wherein the drive members are driven in a reciprocating manner to sequentially compress the respective pressurizing chambers in an alternating, timed sequence to sequentially pass fluid through the separate flow paths and provide substantially continuous fluid flow to the common outlet.

11. The fluid delivery system of claim 10 wherein the at least pressurizing chambers comprises three pressurizing chambers.

12. The fluid delivery system of claim 10 wherein the fluid container comprises an inlet port through which additional fluid or another fluid can be delivered into the fluid container.

13. The fluid delivery system of claim 10 wherein the fluid container comprises one or more outlet ports through which fluid can be delivered to a destination other than the at least two pressurizing chambers.

14. The fluid delivery system of claim 10 wherein the drive mechanism further comprises a closure that is adapted to be moved between an open position and a closed position of the drive mechanism.

15. The fluid delivery system of claim 10 wherein the flexible material of the at least two pressurizing chambers is suitably resilient such that recovery of the flexible material creates a pressure difference between the at least two pressurizing chambers and the fluid container suitable to draw fluid from the fluid container into the at least two pressurizing chambers.

16. An injection system, comprising:
a fluid container;
a pumping mechanism in fluid connection with the fluid container via a connector and comprising at least two generally parallel pressurizing chambers; and
a drive mechanism in operative connection with each of the at least two pressurizing chambers to pump fluid from the fluid container,
wherein each of the at least two pressurizing chambers is formed of a flexible, resilient material adapted to compress thereby pressurizing fluid therewithin,
wherein each of the at least two pressurizing chambers has an input in fluid connection with the fluid container and an output,
wherein each of the at least two pressurizing chambers forms a separate flow path through the pumping mechanism, and
wherein the drive mechanism comprises respective drive members cooperating with the at least two pressurizing chambers to pump fluid from the fluid container and to pressurize fluid within the at least two pressurizing chambers, wherein the drive members are driven in a reciprocating manner to sequentially compress the respective pressurizing chambers in an alternating, timed sequence to sequentially pass fluid through the separate flow paths and provide substantially continuous fluid flow.

17. The injection system of claim 16 wherein the at least two pressurizing chambers comprises three pressurizing chambers.

18. The injection system of claim 16 wherein the fluid container comprises an inlet port through which additional fluid or another fluid can be delivered into the fluid container.

19. The injection system of claim 16 wherein the fluid container comprises one or more outlet ports through which fluid can be delivered to a destination other than the pumping mechanism.

20. The injection system of claim 16 wherein the drive mechanism further comprises a closure that is adapted to be moved between an open position and a closed position of the drive mechanism.

21. The injection system of claim 16 wherein the flexible material of the at least two pressurizing chambers is suitably resilient such that recovery of the flexible material creates a pressure difference between the at least two pressurizing chambers and the fluid container suitable to draw fluid from the fluid container into the at least two pressurizing chambers.

* * * * *

UNITED STATES PATENT AND TRADEMARK OFFICE
CERTIFICATE OF CORRECTION

PATENT NO. : 8,133,205 B2
APPLICATION NO. : 11/942772
DATED : March 13, 2012
INVENTOR(S) : Rhinehart et al.

It is certified that error appears in the above-identified patent and that said Letters Patent is hereby corrected as shown below:

In Column 3, Line 39, delete "fluids." and insert -- fluids --, therefor.

In Column 9, Line 46, delete "100" and insert -- 100. --, therefor.

In Column 10, Line 32, delete "therethrouqh" and insert -- therethrough --, therefor.

In Column 11, Line 41, delete "6,471,674 6,699,219 6,440,107" and insert -- 6,471,674, 6,699,219, 6,440,107 --, therefor.

In Column 12, Line 38, delete "beak-off" and insert -- break-off --, therefor.

IN THE CLAIMS

In Claim 1, Column 14, Line 41, delete "An injection system," and insert -- A fluid delivery system, --, therefor.

In Claim 1, Column 14, Line 51, delete "chambers in fluid connection" and insert -- chambers being in fluid connection, --, therefor.

In Claim 1, Column 14, Line 54, in Claim 1, delete "other," and insert -- other --, therefor.

In Claim 8, Column 15, Lines 28-29, delete "closed position of the drive mechanism." and insert -- closed position. --, therefor.

In Claim 11, Column 16, Line 10, delete "least pressurizing" and insert -- least two pressurizing --, therefor.

In Claim 14, Column 16, Lines 21-22, delete "closed position of the drive mechanism." and insert -- closed position. --, therefor.

Signed and Sealed this
Twelfth Day of February, 2013

Teresa Stanek Rea
*Acting Director of the United States Patent and Trademark Office*

In Claim 20, Column 17, Lines 3-4, delete "closed position of the drive mechanism." and insert -- closed position. --, therefor.